United States Patent [19]
Handley

[11] Patent Number: 5,409,894
[45] Date of Patent: Apr. 25, 1995

[54] METHOD OF PREVENTING BALLOON CATHETERIZATION BLOOD VESSEL DAMAGE

[75] Inventor: Dean A. Handley, Mountain Lakes, N.J.

[73] Assignee: Sandoz Ltd., Basel, Switzerland

[21] Appl. No.: 86,951

[22] Filed: Jul. 6, 1993

Related U.S. Application Data

[63] Continuation of Ser. No. 669,270, Mar. 14, 1991, abandoned.

[51] Int. Cl.$^6$ ............... A61K 38/08; A61K 38/14
[52] U.S. Cl. ........................ 514/8; 530/311; 514/16; 514/17; 514/18
[58] Field of Search ............... 514/16–18, 514/8; 530/311

[56] References Cited

U.S. PATENT DOCUMENTS 5,147,856  9/1992  Ramwell et al. .............. 514/16

*Primary Examiner*—Howard E. Schain
*Attorney, Agent, or Firm*—Robert S. Honor; Melvyn M. Kassenoff; Thomas O. McGovern

[57] ABSTRACT

Somatostatin analogues and derivatives in free form or in pharmaceutically acceptable salt or complex form are useful for preventing or reducing neointimal proleferation following angioplasty.

3 Claims, No Drawings

METHOD OF PREVENTING BALLOON CATHETERIZATION BLOOD VESSEL DAMAGE

This is a continuation of application Ser. No. 07/669,270, filed Mar. 14, 1991, now abandoned This invention relates to an improved method for carting out balloon catheterization of obstructed blood vessels. In particular, this invention relates to preventing neointimal proliferation following balloon catheterization of atherosclerotic blood vessels.

In the treatment of cardiovascular disease, angioplasty has been found to be an effective treatment for clearing the blood vessel of obstructing lesions. Angioplasty however, damages the endothelium and vessel wall, causing further neointimal proliferation of the vessel. This restenosis occurs in the first several months following angioplasty and is a serious complication in 30 to 40% of the patients. Treatments directed toward preventing smooth muscle cell prolification have been unable to significantly reduce the incidence of restenosis.

It has now been found that neointimal proliferation can be reduced or prevented by administering to a subject undergoing angioplasty a restenosis inhibiting amount of:

A. Cyclic peptides having the structure

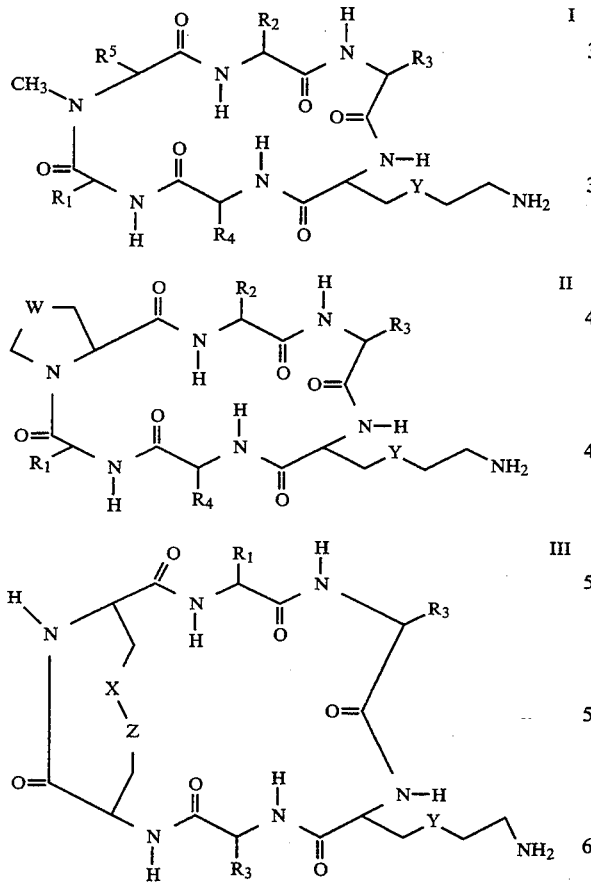

wherein
W is S or $(CH_2)_s$ where s is 0, 1 or 2;
one of X and Z is S and the other is S or $CH_2$;
Y is S or $(CH_2)_t$ where t is 0, 1 or 2;
each of $R_1$ and $R_2$ independently of the other, is $C_{1-5}$ alkyl, benzyl, benzyl having one or two $C_{1-5}$ alkyl, halogen, hydroxy, amino, nitro, and/or $C_{1-5}$ alkoxy substituents, or $C_{1-5}$ alkyl substituted with a 5- or 6-membered heterocyclic ring;

$R_3$ is 3-indolylmethyl, either unsubstituted or having $C_{1-5}$ alkyl, $C_{1-5}$ alkoxy or halogen substitution;

$R_4$ is $C_{1-5}$ alkyl, $C_{1-5}$ hydroxyalkyl, benzyl, carboxy-($C_{1-5}$ alkyl), amino ($C_{1-5}$ alkyl) or benzyl having a $C_{1-5}$ alkyl, halogen, hydroxy, amino, nitro and/or $C_{1-5}$ alkoxy substituent;

$R_5$ is $C_{1-5}$ benzyl, or benzyl having a $C_{1-5}$ alkyl, halogen, hydroxy, amino, nitro, and/or $C_{1-5}$ alkoxy substituent.

Examples of $C_{1-5}$ alkyl groups are methyl, ethyl, propyl, iso-propyl, butyl, sec-butyl and pentyl; examples of $C_{1-5}$ alkoxy groups are methoxy, ethoxy, propoxy, iso-propoxy, butoxy, tert-butoxy, and pentoxy; halogens are fluorine, chlorine, bromine, or iodine: and the term "5- or 6-membered heterocyclic ring" represents such rings with one or two oxygen, nitrogen and/or suphur heteroatoms, e.g. imidazole, furan, thiazote, pyrazole and pyridine.

In the compounds of Formulae I, II and III, there are several asymmetric centres which lead to the existence of optical isomers for such compounds. For each of the asymmetric centres of the various amino acids which make up these cyclic hexapeptides, both the D and L configurations are included.

The following are representative cyclic hexapeptide analogues of somatostatin of Formulae I, II and III:

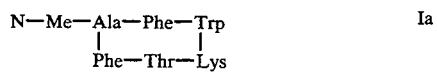

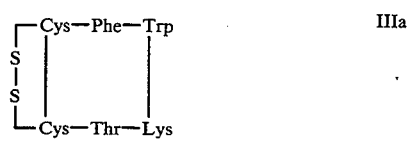

Preferred Formula I compounds are:
1) Cyclo-(N-Me-Ala-Tyr-D-Trp-Lys-Thr-Phe)
2) Cyclo-(N-Me-Ala-Phe-D-Trp-Lys-Thr-Phe)
3) Cyclo-(N-Me-Ala-Phe-L-Trp-Lys-Thr-Phe)
4) Cyclo-(N-Me-Ala-Phe-D-Trp-Lys-Thr-p-Cl-Phe)
5) Cyclo-(N-Me-Ala-Phe-D-S-F-Trp-Lys-Thr-Phe)
6) Cyclo-(N-Me-Ala-Phe-L-S-F-Trp-Lys-Thr-Phe)
7) Cyclo-(N-Me-Ala-Phe-D-Trp-Lys-Ser-Phe)
8) Cyclo-(N-Me-Ala-Tyr-D-Trp-Lys-Val-Phe)
9) Cyclo-(N-Me-Ala-Tyr-D-Trp-Lys-Val-Trp)
10) Cyclo-(N-Me-Ala-Tyr-L-Trp-Lys-Val-Phe)
11) Cyclo-(Ser-Ala-N-Me-Phe-His-D-Trp-Lys)

Preferred Formula II compounds are:
12) Cyclo-(Pro-Tyr-D-Trp-Lys-Thr-Phe)
13) Cyclo-(Pro-Phe-D-Trp-Lys-Thr-Phe)
14) Cyclo-(Pro-Phe-L-Trp-Lys-Thr-Phe)
15) Cyclo-(Pro-Phe-D-Trp-Lys-Thr-p-Cl-Phe)
16) Cyclo-(Pro-Phe-D-5-F-Trp-Lys-Thr-Phe)
17) Cyclo-(Pro-Phe-L-5-F-Trp-Lys-Thr-Phe)
18) Cyclo-(Pro-Phe-D-Trp-Lys-Ser-Phe)

Preferred Formula III compounds are:

19) Cyclo-(Cys—Cys—Tyr—D—Trp—Lys—Thr)

20) Cyclo-(Cys—Cys—Tyr—D—Trp—Lys—Val)

21) Cyclo-(Cys—Cys—Tyr—L—Trp—Lys—Val)

22) Cyclo-(Cys—Cys—Phe—D—Trp—Lys—Thr)

23) Cyclo-(Cys—Cys—Phe—L—Trp—Lys—Thr)

24) Cyclo-(Cys—Cys—His—D—Trp—Lys—Thr)

25) Cyclo-(Cys—Cys—His—D—Trp—Lys—Val)

26) Cyclo-(Cys—Cys—Ala—Phe—D—Trp—Lys—Thr).

B. Compounds of formula IV

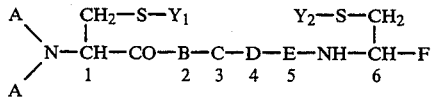

wherein

A is $C_{1-12}$ alkyl, $C_{7-10}$ phenylalkyl or a group of formula RCO—, whereby
  i) R is hydrogen, $C_{1-11}$ alkyl, phenyl or $C_{7-10}$ phenylalkyl, or
  ii) RCO— is
    a) an L- or D-phenylalanine residue optionally ring-substituted by halogen, $NO_2$, $NH_2$, OH, $C_{1-3}$ alkyl and/or $C_{1-3}$ alkoxy
    b) the residue of a natural or synthetic α-amino acid other than defined under a) above or of a corresponding D-amino acid, or
    c) a dipeptide residue in which the individual amino acid residues are the same or different and are selected from those defined under a) and/or b) above, the αamino group of amino acid residues a) and b) and the N-terminal amino group of dipeptide residues c) being optionally mono-or di-$C_{1-12}$ alkylated, A' is hydrogen or, when A is $C_{1-12}$ alkyl or $C_{7-10}$ phenylalkyl, also $C_{1-12}$ alkyl or $C_{7-10}$ phenylalkyl, $Y_1$ and $Y_2$ represent together a direct bond or each of $Y_1$ and $Y_2$ is independently hydrogen or a radical of formulae (1) to (5)

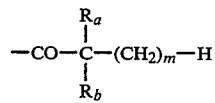 (1)

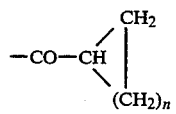 (2)

—CO—NHR$_c$ (3)

—CO—NH—CH—COOR$_e$ (4)
         |
         R$_d$

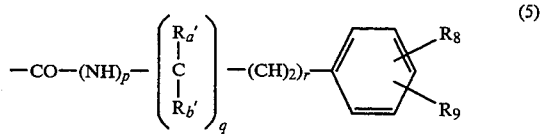 (5)

wherein
R$_a$ is methyl or ethyl
R$_b$ is hydrogen, methyl or ethyl
m is a whole number from 1 to 4
n is a whole number from 1 to 5
R$_c$ is ($C_{1-6}$)alkyl
R$_d$ represents the substituent attached to the α-carbon atom of a natural or synthetic α-amino acid (including hydrogen)
R$_e$ is ($C_{1-5}$)alkyl
R$_a'$ and R$_b'$ are independently hydrogen, methyl or ethyl,
R$_8$ and R$_9$ are independently hydrogen, halogen, ($C_{1-3}$)alkyl or ($C_{1-5}$)alkoxy,
p is 0 or 1,
q is 0 or 1, and
r is 0, 1 or 2,
B is -Phe- optionally ring-substituted by halogen, $NO_2$, $NH_2$, OH, $C_{1-3}$alkyl and/or $C_{1-3}$alkoxy, or 3-(2-naphthyl)-alanine
C is (L)-Trp- or (D)-Trp- optionally α-N-methylated and optionally benzene-ring-substituted by halogen, $NO_2$, $NH_2$, OH, $C_{1-3}$ alkyl and/or $C_{1-3}$ alkoxy
D is Lys, Lys in which the side chain contains O or S in β-position, γF-Lys, δF-Lys or Orn, optionally α-N-methylated, or a 4-aminocyclohexylAla or 4-aminocyclohexylGly residue
E is Thr, Ser, Val, Phe, Tyr, Ile or an aminoisobutyric or aminobutyric acid residue p1 F is —COOR$_7$, —CH$_2$OR$_{10}$,

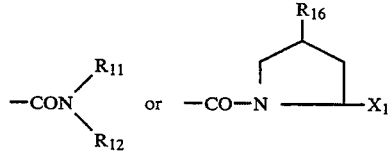

wherein
R$_7$ is hydrogen or $C_{1-3}$alkyl,
R$_{10}$ is hydrogen or the residue of a physiologically acceptable, physiologically hydrolysable ester,
R$_{11}$ is hydrogen, $C_{1-3}$alkyl, phenyl or $C_{7-10}$ phenylalkyl,
R$_{12}$ is hydrogen, $C_{1-3}$alkyl or a group of formula —CH(R$_{13}$)—X$_1$,
R$_{13}$ is —(CH$_2$)$_2$—OH, —(CH$_2$)$_3$—OH, or —CH(CH$_3$)OH or represents the substituent attached to the α-carbon atom of a natural or synthetic α-amino acid (including hydrogen) and
X$_1$ is a group of formula —COOR$_7$, —CH$_2$OR$_{10}$ or

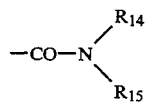

wherein
$R_7$ and $R_{10}$ have the meanings given above,
$R_{14}$ is hydrogen or $C_{1-3}$ alkyl and
$R_{15}$ is hydrogen, $C_{1-3}$ alkyl, phenyl or $C_{7-10}$ phenylalkyl, and
$R_{16}$ is hydrogen or hydroxy,
with the proviso that
when $R_{12}$ is $CH(R_{13})$—$X_1$ then $R_{11}$ is hydrogen or methyl, or when $Y_1$ and $Y_2$ are a direct bond and $X_1$ is —$COOR_7$ or —$CO$—$NR_{14}R_{15}$, A is a residue b) or c) as defined above,
wherein the residues B, D and E have the L-configuration, and the residues in the 2- and 7-position and any residues $Y_1$ 4) and $Y_2$ 4) each independently have the (L)- or (D)- configuration, in free form or in pharmaceutically acceptable salt or complex form.

In the compounds of formula IV, the following significances are preferred either individually or in any combination or sub-combination:

1. A is $C_{7-10}$ phenylalkyl, especially phenethyl, or a group of formula RCO. Preferably A is a group of formula RCO.
   1.1. Preferably R is $C_{1-11}$ alkyl or $C_{7-10}$ phenylalkyl, especially $C_{7-10}$ phenylalkyl, more especially phenethyl, or
   RCO has the meanings a), b) or c).
   1.2. When RCO has the meanings a), b) or c), the α-amino group of amino acid residues a) and b) and the N-terminal amino group of dipeptide residues c) is preferably non-alkylated or mono-$C_{1-12}$ alkylated, especially -$C_{1-8}$ alkylated, more especially -methylated. Most preferably the N-terminal is non-alkylated.
   1.3. When RCO has the meaning a) this is preferably a') an L- or D-phenylalanine or -tyrosine residue optionally mono-N-$C_{1-12}$ alkylated. More preferably a') is an L- or D-phenylalanine residue or an L- or D-N-($C_{1-8}$-alkyl)-phenylalanine residue. Most preferably a') is a D-phenylalanine or D-N-($C_{1-8}$ alkyl)-phenylalanine residue, especially a D-phenylalanine or D-(N-methyl)-phenylalanine residue.
   1.4. When RCO has the meaning b) or c) the defined residue is preferably lipophilic. Preferred residues b) are thus b') α-amino acid residues having a hydrocarbon side chain, e.g. alkyl with 3, preferably 4, or more C atoms, e.g. up to 7 C-atoms, naphthylmethyl or heteroaryl, e.g. 3-(2- or 1-naphthyl)-alanine residue or tryptophane residue, said residues having the L- or D-configuration, and preferred residues c) are dipeptide residues in which the individual amino acid residues are the same or different and are selected from those defined under a') and b') above.
   Example of a residue c) is e.g. 3-(2-naphthyl)-alanine residue.
   1.5. Most preferably RCO has the meaning a) especially the meaning a').
2. B is B', where B' is Phe or Tyr.
3. C is C', where C' is (D)Trp.
4. D is D', where D' is Lys, MeLys or Lys(ε-Me), especially Lys.
5. E is E', where E' is the residue of a natural α-amino acid, for example Val or Thr, especially Thr.
6. F is F', where F'' is a group of formula

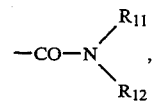

especially a group of

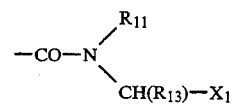

(in which case $R_{11}$=H or $CH_3$). In the latter case the moiety —$CH(R_{13})$—$X_1$ preferably has the L-configuration.
   6.1. $R_{11}$ is preferably hydrogen.
   6.2. As the substituent attached to the α-carbon atom of a natural amino acid (i.e. of formula $H_2N$—$CH(R_{13})$—$COOH$), $R_{13}$ is preferably —$CH_2OH$, —$CH(CH_3)$—OH, isobutyl or butyl, or $R_{13}$ is —$(CH_2)_2$—OH or —$(CH_2)_3$—OH. It is especially —$CH_2OH$ or —$CH(CH_3)OH$.
   6.3. $X_1$ is preferably a group of formula —$CH_2$—$OR_{10}$
7. As the residue of a physiologically acceptable, physiologically hydrolysable ester $R_{10}$ is preferably HCO, $C_{2-12}$ alkylcarbonyl, $C_{8-12}$ phenylalkylcarbonyl or benzoyl.
8. Preferably the residues in the 2- and 7-positions have the L-configuration.
9. Preferably $Y_1$ and $Y_2$ together represent a direct bond.

Suitable derivatives bearing at least one sugar residue are e.g. compounds of formula IV including the compound octreotide bearing a sugar residue preparable by an Amadori or Heyns rearrangement from a natural or a synthetically accessible mono-, di- or oligosaccharide e.g. as disclosed in WO 88/02756, the contents of which being incorporated herein by reference.

Preferred sugar derivatives are the compounds of formula IV which have a sugar residue on the N-terminal amino group, e.g. a residue of formula

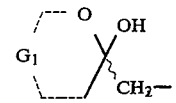

which is the deoxy residue of a ketose, e.g. a radical obtainable by means of an Amadori rearrangement from a natural or synthetically accessible mono-, di- or oligosaccharide, or a residue of formula

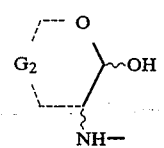

which is the deoxy residue of an aldose, e.g. a radical obtainable by means of a Heyns rearrangement from a natural or a synthetically accessible mono-, di- or oligoketose, or a residue of formula

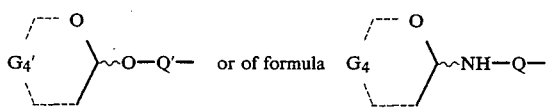

which are each independently a sugar residue and linked to the N-terminal amino group by a coupling group Q or Q', e.g. the radical of a dicarboxylic acid or $C_bH_{2b}$—CO-radical wherein b is 1 to 6.

A particularly preferred compound is

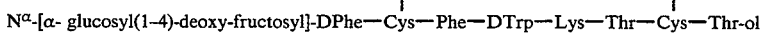

(referred to as compound of formula IVc) in free form or in pharmaceutically acceptable salt or complex form.

C. Compounds of formulae V to IX

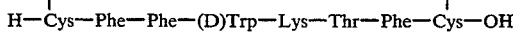    V

[see Vale et.al., Metabolism, 27, Supp. 1, 139, (1978)]

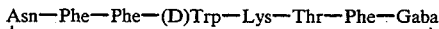    VI

[see European Patent Publication No 1295 and Application No. 78 100 994.9]

    VII

[see R. F. Nutt et al. Klin. Wochenschr. (1986) 64 (Suppl. VII) 71–73.

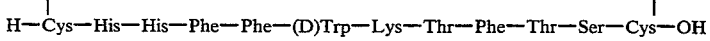    VIII (see EP-A-200,188) Cyclo-(DTrp-Lys-Val-Phe-NMeAla-Tyr) (see EP-A-70,021)

The contents of all the above publications including the specific compounds are specifically incorporated herein by reference.

The compounds of the invention may exist e.g. in free form, salt form or in the form of complexes thereof. Acid addition salts may be formed with e.g. organic acids, polymeric acids and inorganic acids. Such acid addition salt forms include e.g. the hydrochlorides and acetates. Complexes are e.g. formed from compounds of the invention on addition of inorganic substances, e.g. inorganic salts or hydroxides such as Ca- and Zn-salts, and/or an addition of polymeric organic substances. The salts and complexes exhibit the same order of activity as the free base form.

Somatostatin analogues and derivatives are mainly disclosed as having an inhibitory effect on growth hormone, glucagon and insulin secretion.

The known compound of formula IV, octreotide, which has the structure:

in free form or in pharmaceutically acceptable salt or complex form is the preferred compound of the invention.

The above analogs are useful in preventing restenosis following balloon catheterization as indicated in Sprague-Dawley rats weighing 475 to 550 grams given 1 to 100 μg/kg s.c. twice a day essentially in accordance with the procedure described by Handley et al; SUPRESSION OF RAT CAROTID LESION DEVELOPMENT BY THE CALCIUM CHANNEL BLOCKER PN 200-110; AM. J. PATHOL.; VOL. 124; NO. 1; (JULY 1986).

The amount of compound of formula (I) administered for the above use will vary depending on the compound used and the individual undergoing treatment. However, satisfactory results are obtained when administered at daily dosages of from 0.5 to 1000 μg/kg of animal body weight. The compounds are generally administered in individual dosages ranging from about 25 micrograms to about 1000 micrograms per day. The preferred compound octreotide is administered subcutaneously at daily doses of from about 50 to about 1500 micrograms, preferably about 150 to about 750 micrograms, although higher doses may be required by some individuals. In most cases, however, octreotide is administered subcutaneously in unit doses of about 10 to about 750 micrograms, preferably 50 to about 375 milligrams 2 to 4 times daily. Normally,, the initial daily dose of octreotide is about 100 to 600 micrograms per day s.c. in two to four divided doses for the first two weeks.

The dosage is gradually increased to about 450 to 750 micrograms in two to four divided doses if required to decrease somatomedin C levels in plasma. The sugar derivative of octreotide, compound IVc above, is preferably administered in an oral form at dosages of from 2 micrograms to 20 milligrams p.o., preferably 300 to 5000 micrograms p.o., in unit dosage forms containing 5 micrograms to 10 milligrams of compound IVc. In carrying out this invention, it is preferred that the subject undergoing the balloon catheterization procedure, be started on the compound of the invention 3 to 5 days, more preferably 5 days, before the procedure commences and the administration of the compound continued for 14 to 60 days after completion of the balloon catheterization.

The salts and complexes exhibit the same order of activity as the base compound.

The active ingredient of the invention are administered enterally or preferably parenterally or subcutaneously admixed with conventional pharmaceutical carriers. They may be administered enterally in the form of tablets or capsules or preferably, parenterally as solutions, e.g., sterile injectable solution, suspensions, e.g., aqueous suspension, or in depot form, in which the active ingredient is coated by known techniques to delay disintegration and absorption and thereby provide a sustained action over large periods-of time. The compositions are formulated as disclosed in the art. These pharmaceutical preparations may contain up to about 90% of the active ingredients in combination with the carrier or adjuvant.

The following is illustrative of the preparation of compositions in accordance with the invention.

|  | Concentration per ml 1. Ampoules | | | |
|---|---|---|---|---|
|  | Ex. 1 | Ex. 2 | Ex. 3. | Ex. 4 |
| Octreotide* | 0.05 mg | 0.1 mg | 0.2 mg | 0.5 mg |
| Mannitol | 45.0 mg | 45.0 mg | 45.0 mg | 45.0 mg |
| Lactic acid (88%) | 3.4 mg | 3.4 mg | 3.4 mg | 3.4 mg |
| Sodium hydrogeno-carbonate | to pH 4.2 | to pH 4.2 | to pH 4.2 | to pH 4.2 |
| Water(inject. grade) | to 1 ml | to 1 ml | to 1 ml | to 1 ml |
| Carbon dioxide | q.s. | q.s. | q.s. | q.s. |

|  | 2. Vials |
|---|---|
|  | Ex. 6 |
| Octreotide* | 0.2 mg |
| Mannitol | 45.0 mg |
| Lactic acid (88%) | 3.4 mg |
| Phenol | 5.0 mg |
| Sodium hydrogeno-carbonate | to pH 4.2 |
| Water (injection grade) | to 1 ml |
| Carbon dioxide | q.s. |

*given as the acetate peptide content 87 percent.
The compositions are prepared by standard techniques, e.g. in charges of 50 liters to provide about 43 000 ampoules of 1 ml of 8400 vials under carbon dioxide gassing. The compositions are filtered (e.g. through 0.2 micron holes at 0.5 bar) and introduced in the ampoules or vials under aseptic conditions.

The effect of the preferred compound, octreotide is determined using male Sprague-Dawley rats, weighing 475 to 550 grams, as indicated above, which are housed and allowed to acclimate for 1 week before the start of the experiment. A constant-formula rodent laboratory food and water are available ad libitum. The groups consisted of animals given 25 µg/kg/day (n=6) and 100 µg/kg/day (n=8) of octreotide acetate in 10% ethanol water subcutaneously and vehicle-treated controls (n=16). Administration begins 4 days before catheterization and continues for 14 days afterwards. The animals are randomized into three groups for catheterization and are weighed every other day throughout the study. Plasma somatomedin C levels are measured in animals selected at random by standard procedures with Nichols Inst. RIA. The method of carotid balloon catheterization as modified from the original protocol by Baumgartner is described in Clowes AW, Reidy MA, Clowes MM: Mechanisms of stenosis after arterial injury, Lab Invent: 1983; 49;208–215, and Baumgartner HR: Eine neue Methode zur Erzeugung yon Thromben durch Überdehnung der Gefasswand; Z Gesamte Exp Med; 1963; 137:235. The carotid artery is completely deendothelialized by the procedure. Animals are sacrificed 14 days after angioplasty in the same sequence as the catheterization. Thirty minutes before fixation the animals are given an injection of a 2.25% Evans blue dye solution (1.5 mg/kg intravenously) to differentiate between the denuded and reendothelialized areas. Whole-body (beating heart) perfusion fixations (90–110 mmHg) are then performed on anesthetized (sodium pentobarbital; 50.0 mg/kg intraperitoneally) animals with the use of 1% glutaraldehyde in 0.15M sodium cacodylate buffer (pH 7.4, 37 C, 410 mOsm) followed by 3% gluteraldehyde in 0.15M sodium cacodylate. Thoracic aorta flow is restricted to optimize carotid perfusion. Successful fixation is judged by upper-body rigidity and an absence of blood from the large arteries. The fixed carotid is removed and cut into three segments (distal, central, proximal). Only the central segment tissue is processed, which includes 18 hours in 3% buffered glutaraldehyde, buffer rinsing, dehydration in an ascending ethanol series, and infiltration with Spurr's resin. The samples are embedded with cross-sectional orientation so that sectioning (0.5µ) includes blue areas that have not reendothelialized and show continued proliferative responses. A two-step polychromatic strain utilizing toluidine blue and 1.0% basic fuchsin permits histologic differentiation of nuclear, cytoplasmic, and extracellular connective matrix components.

All light-microscopic histology slides are randomized, encoded, and evaluated with the use of a Zeiss standard microscope and the Videoplan computerized image analyzer. Vessel measurements of maximum lesion height and lesion areas are recorded. Image calibration and magnification checks are performed for every group of slides analyzed, and analysis of groups is done by parametric and nonparametric statistical methods. In the above test, it is determined that compared with the controls, octreotide reduces maximal lesion height and lesion area by 21% and 24.7% respectively at 25 µg/kg and 14% and 16% respectively at 100 µg/kg. Plasma somatomedin C levels are reduced from 8,000 to 11,000 units/ml of plasma to about 1,200 units/ml by day 3 and stay at that level for the entire study.

What is claimed:

1. A method of preventing or reducing neointimal proliferaton in a subject undergoing angioplasty, which comprises administering to said subject an effective restenosis inhibiting amount of

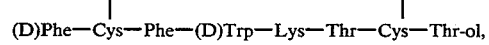
(D)Phe—Cys—Phe—(D)Trp—Lys—Thr—Cys—Thr-ol, in free form or in pharmaceutically acceptable salt or complex form.

2. A method of preventing or reducing neointimal proliferation in a subject undergoing angioplasty, which comprises administering to said subject an effective restenosis inhibiting amount of Na—[α-glucosyl(1-4)-deoxy-fructosyl]-

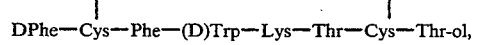
DPhe—Cys—Phe—(D)Trp—Lys—Thr—Cys—Thr-ol, in free form or in pharmaceutically acceptable salt or complex form.

3. A method of preventing or reducing neointimal proliferation in a subject undergoing angioplasty according to claim 1, which comprises administering to said subject a restenosis inhibiting amount of

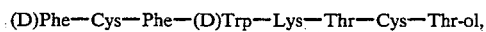
(D)Phe—Cys—Phe—(D)Trp—Lys—Thr—Cys—Thr-ol, in acetate salt form.

* * * * *